United States Patent
Schäfer et al.

(10) Patent No.: US 9,492,362 B2
(45) Date of Patent: Nov. 15, 2016

(54) AQUEOUS OXIDIZING COMPOSITION

(71) Applicant: KAO GERMANY GMBH, Darmstadt (DE)

(72) Inventors: Sabine Schäfer, Rüsselsheim (DE); Jonathan Wood, Weinheim (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 14/419,126

(22) PCT Filed: Aug. 9, 2013

(86) PCT No.: PCT/EP2013/066718
§ 371 (c)(1),
(2) Date: Feb. 2, 2015

(87) PCT Pub. No.: WO2014/026927
PCT Pub. Date: Feb. 20, 2014

(65) Prior Publication Data
US 2015/0238398 A1    Aug. 27, 2015

(30) Foreign Application Priority Data
Aug. 13, 2012 (EP) .................................... 12180207

(51) Int. Cl.
| | | |
|---|---|---|
| A61Q 5/04 | (2006.01) |
| A61Q 5/10 | (2006.01) |
| A61K 8/23 | (2006.01) |
| A61K 8/19 | (2006.01) |
| A61K 8/22 | (2006.01) |
| A45D 7/04 | (2006.01) |
| A45D 7/00 | (2006.01) |
| A45D 19/00 | (2006.01) |

(52) U.S. Cl.
CPC . *A61K 8/23* (2013.01); *A45D 7/04* (2013.01); *A61K 8/19* (2013.01); *A61K 8/22* (2013.01); *A61Q 5/04* (2013.01); *A61Q 5/10* (2013.01); *A45D 2007/001* (2013.01); *A45D 2019/0066* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 7,799,095 B2 | 9/2010 | Mario et al. | |
| 8,613,778 B2* | 12/2013 | Wood ................ | A61K 8/19 8/405 |
| 2006/0246022 A1* | 11/2006 | Bureiko ............. | A61K 8/0291 424/62 |
| 2009/0151087 A1 | 6/2009 | Mario et al. | |
| 2009/0202598 A1* | 8/2009 | Kravtchenko ....... | A61K 8/064 424/401 |
| 2011/0146007 A1* | 6/2011 | Goget ................ | A61K 8/31 8/407 |
| 2011/0220140 A1* | 9/2011 | Wood ................ | A61K 8/22 132/205 |

FOREIGN PATENT DOCUMENTS

| | | |
|---|---|---|
| EP | 2 011 474 A1 | 1/2009 |
| EP | 2246097 * | 11/2010 |
| EP | 2 468 241 A1 | 6/2012 |
| GB | 758 611 A | 10/1956 |
| GB | 852 102 A | 10/1960 |
| WO | 99/43781 A1 | 9/1999 |

OTHER PUBLICATIONS

International Search Report dated Oct. 22, 2013, Nov. 4, 2013.

* cited by examiner

*Primary Examiner* — Jyothsna Venkat
(74) *Attorney, Agent, or Firm* — Norris McLaughlin & Marcus PA

(57) ABSTRACT

Present invention relates to an aqueous oxidizing composition with improved peroxide stability. The aqueous compositions of the present invention comprises at least oxidizing agent, at least one magnesium salt and have a pH between 1 and 5.

13 Claims, No Drawings

AQUEOUS OXIDIZING COMPOSITION

This application is a 371 application of PCT/EP2013/066718 filed Aug. 9, 2013, which claims foreign priority benefit under 35 U.S.C. §119 of European Application No. 12180207.8 filed Aug. 13, 2012, the disclosures of which are incorporated herein by reference.

Present invention relates to an aqueous oxidizing composition with improved peroxide stability.

Oxidizing compositions are used as hair cosmetics for lightening hair colour, in hair dyeing processes for achieving colours from oxidative dye precursors and coupling substances and also in permanent shaping processes wherein after opening the disulfide bonds, building of the disulfide bonds is done with the aid of an aqueous oxidizing composition in order to fix the new shape.

Oxidizing agents included in such compositions undergo decomposition wherein oxygen is produced which leads to increase in internal pressure of the packaging material wherein such compositions are stored. This result in problems such as swelling of the packaging material and therefore the vessel may not be simply kept standing on the bench and it may also lead to a product splash when opening the lid and/or closure of the vessel. These problems are aggravated especially when such compositions have relatively high viscosity as oxygen cannot easily leave the compositions and be stored at upper space in the vessel.

Furthermore, stabilization of oxidizing agent leads to less hair damage as reactive oxygen concentration in the composition and/or in the mixture is reduced so that excessive oxygen available does not react with hair.

There is an explicit need for measures realizing higher peroxide stability in order to overcome the above mentioned drawbacks and at least reducing the risks coming from peroxide instability.

There are substances known to have peroxide stabilizing effect. Use of these substances alone is also common in hair cosmetic practice. These substances are salicylic acid, acetaminophen and oxyquinoline and its salts. Use of any of these substances even at elevated concentration however has not resulted in improvement of peroxide stability and solution to the above described problems.

Inventor of the present invention has found out that use of a magnesium salt has surprisingly provided improved peroxide stability and therefore the above described problems were solved, especially it has been observed that hair treated with aqueous oxidizing composition of the present invention is less damaged.

Therefore, the first object of the present invention is an aqueous composition comprising at least one oxidizing agent, at least one magnesium salt and having a pH between 1 and 5.

The second object of the present invention is an aqueous composition comprising at least one oxidizing agent, at least one inorganic magnesium salt and has a pH between 1 and 5.

The third object of the present invention is use of the composition of the present invention for treating hair.

The fourth object of the present invention is the use of at least one magnesium salt, especially inorganic magnesium salt for stabilizing peroxide, especially hydrogen peroxide, in aqueous composition.

The fifth object of the present invention is a kit for treating hair comprising two or more compositions wherein one of the compositions is an aqueous composition comprising at least one oxidizing agent, at least one magnesium salt, especially inorganic magnesium salt and having a pH between 1 and 5.

Compositions of the present invention are aqueous compositions and therefore comprise at least 45% by weight water, preferably between 50 and 90%, more preferably between 55 and 85% and most preferably between 60 and 80% by weight water calculated to the total composition.

Composition of the present invention has an acidic pH, between 1 and 5, preferably between 1.5 and 4.5, more preferably between 2 and 4, and most preferably between 2.5 and 3.5, all values are included. The pH of the compositions is adjusted by using commonly used organic and/or inorganic acids, preferably with inorganic acids and their salts and more preferably with phosphoric acid and its salts.

Compositions comprise at least one oxidizing agent. Suitable ones are hydrogen peroxide, urea peroxide, melamin peroxide or perborate salts. The most preferred is hydrogen peroxide. At least one oxidizing agent is comprised in the aqueous compositions at a concentration in the range of 0.1 to 25%, preferably 0.5 to 20%, more preferably 0.5 to 15% and in particular 1 to 12% by weight calculated to the total composition.

Composition of the present invention comprises at least one magnesium salt. Suitable ones are organic and inorganic salts such as magnesium aluminium borosilicate, magnesium aspartate, magnesium borate, magnesium bromate, magnesium bromide, magnesium benzoate, magnesium acetate, magnesium carbonate, magnesium citrate, magnesium clorate, magnesium dihydrogen phosphate, magnesium fluoride, magnesium formate, magnesium hydroxide, magnesium iodide, magnesium lactate, magnesium mandalate, magnesium monofluorophosphate, magnesium oxalate, magnesium oxide, magnesium perborate, magnesium phosphate, magnesium propionate, magnesium pyrophosphate, magnesium salicylate, magnesium silicate, magnesium chloride, magnesium sulphate, magnesium nitrate and magnesium tartarate.

Preferred are magnesium benzoate, magnesium acetate, borate, magnesium bromate, magnesium bromide, magnesium carbonate, magnesium citrate, magnesium dihydrogen phosphate, magnesium fluoride, magnesium hydroxide, magnesium lactate, magnesium monofluorophosphate, magnesium oxide, magnesium phosphate, magnesium propionate, magnesium pyrophosphate, magnesium salicylate, magnesium silicate, magnesium tartarate, magnesium phosphate, magnesium iodide, magnesium chloride, magnesium sulphate, magnesium nitrate and magnesium bromide.

More preferred magnesium acetate, borate, magnesium bromate, magnesium bromide, magnesium carbonate, magnesium citrate, magnesium dihydrogen phosphate, magnesium fluoride, magnesium hydroxide, magnesium lactate, magnesium oxide, magnesium phosphate, magnesium propionate, magnesium pyrophosphate, magnesium silicate, magnesium tartarate, magnesium chloride, magnesium iodide, magnesium sulphate, magnesium nitrate and magnesium bromide.

The most preferred are inorganic magnesium salts which are magnesium carbonate, borate, magnesium bromate, magnesium bromide, magnesium dihydrogen phosphate, magnesium fluoride, magnesium hydroxide, magnesium oxide, magnesium phosphate, magnesium pyrophosphate, magnesium sulphate, magnesium nitrate, magnesium chloride, magnesium iodide and magnesium bromide. Magnesium sulphate is particularly preferred because of its outstanding effect.

Concentration of at least one magnesium salt in the compositions of the present invention is between 0.1 and 20%, preferably between 0.5 and 15%, more preferably between 0.75 and 10% and most preferably between 1 and 7.5% by weight calculated to total composition prior to mixing with oxidizing lotion.

Compositions may comprise additional one or more peroxide stabilizing agents selected from salicylic acid and/or it salts, acetaminophen and oxyquinoline and/or its salts. Suitable salicylate salts are sodium and/or potassium salts and suitable oxyquinoline salts are oxyquinoline benzoate and oxyquinoline sulphate. The preferred total concentration of one or more additional peroxide stabilizing agent is in the range of 0.001 to 1%, more preferably 0.002 to 0.75% most preferably 0.005 to 0.5% by weight calculated to the total composition.

Compositions of the present invention may be in the form of solutions, thickened aqueous compositions, gels, two phase composition and emulsions.

The solutions usually do not comprise any additional ingredient other than peroxide, one or more magnesium salts, pH adjusting agents and water.

The thickened aqueous compositions and/or gels comprise at least one thickening agent such as polymers of any nature which may have thickening effect at the pH of the compositions which is mentioned above. With the term thickening agent it is meant that the compound has a thickening effect in the compositions as disclosed above. Non-limited examples are cellulose derivatives such as hydroxyethylcellulose, hydroxymethylcellulose, polyquesternium-10, xanthan gum and their derivatives. Additional thickeners may be, depending on the pH, acrylate type of polymers and especially the ones which have appropriate thickening effect in acidic pH range such as the one known with the trade name Carbopol Aqua SF-1. The concentration of the thickening agent may be in the range of 0.01 to 5% depending on the required consistency.

Compositions of the present invention are preferably emulsions and comprise therefore fatty alcohol, oil and one or more surfactants as emulsifiers.

The fatty alcohols preferred are according to the following general structure

$R_1$—OH wherein $R_1$ is a linear or branched, saturated or unsaturated alkyl chain with 12 to 22 C atoms. Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 1 to 20%, more preferably 1.5 to 15% and most preferably 1.5 to 10% by weight calculated to total composition.

Compositions comprise preferably oil, more preferably natural oil and most preferably natural triglycerides. Concentration of oil varies between 0.1 and 25%, preferably 0.5 and 25% and more preferably 1 and 20%, most preferably 2 and 20%, in particular 2.5 and 15% by weight calculated to the total composition.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil. Preferred are argan oil, shea butter oil, karite oil, olive oil, almond oil, avocado oil, ricinus oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, ricinus oil, coconut oil, palm oil, sesame oil, peanut oil, sunflower oil, peach kernel oil, wheatgerm oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil, shea butter oil and karite oil which may be comprised as a single oil component or in admixture with each other.

Further suitable oil components are natural oils such as paraffin oil.

Further suitable ones are synthetic oils such as silicones known with CTFA adopted name dimethicone, cyclomethicone, and arylates silicones such as phenyl trimethicone which are available commercially from Dow Corning.

Further suitable synthetic oils are fatty acid fatty alcohol esters such as octyl palmitate, isocetyl palmitate, isopropyl palmitate and octyl stearate.

Compositions preferably comprise at least one surfactant as an emulsifier. Suitable surfactants are non-ionic, cationic and anionic ones. Most preferred are non-ionic and cationic surfactants.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$—$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N-$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants. Preferred are alkyl sulphates or alkyl ether sulphates and the most preferred are alkyl ether sulphates.

Further surfactants in the compositions according to the invention are nonionic surfactants. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates. Further nonionic surfactants preferred in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 25, preferably about 10 and about 20. The most preferred is ceteth, steareth and ceteareth with 20 to 35 ethoxy groups and ceteareth-30 is particularly preferred.

Compositions preferably comprise a cationic surfactant and especially a monoalkyl cationic surfactant according to the general structure

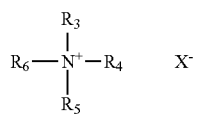

where $R_3$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$, $R_5$ and $R_6$ are lower alkyl chain with 1 to 4 Carbon atoms which may be substituted with one or more of OH groups, and X is typically chloride, bromide, methosulfate.

Typical examples of those ingredients are cetyl trimethyl ammonium chloride, stear trimonium chloride, palmitoyl trimonium chloride, stearyl trimonium chloride, stearamidopropyl trimonuim chloride and oleoylethyl trimethyl ammonium methosulfate. The most preferred are cetyl trimethly ammonium chloride, stear trimonium chloride and palmitoyl trimonium chloride. Cetyl trimethyl ammonium is particularly preffered.

Compositions preferably comprise at least one polyol. With the term polyol those compounds are meant which comprise two or more OH groups in their molecule. Suitable non-limited examples are propylene glycol, butyleneglycol, panthenol, and glycerine. The most preferred is glycerine. Concentration of at least one polyol is in the range of 0.1 to 20%, preferably 1 to 15% and more preferably 2 to 10% by weight calculated to the total composition.

Compositions preferably comprise additionally at least one chelating agent. In principal any chelating agent known in the field of cosmetics is suitable for the compositions of the present invention. Preferred are ethylene diamine tetraacetic acid (EDTA) etidronic acid, galactaric acid, gluconic acid and therei respective salts. Most preferred are diamine tetraacetic acid (EDTA) etidronic acid and gluconic acid and their respective salts and also their mixtures.

Total concentration of chelating agents in the compositions of the present invention is in the range of 0.01 to 2.5%, preferably 0.02 to 2%, more preferably 0.05 to 1.5% and most preferably 0.1 to 1% by weight calculated to the total composition.

Aqueous oxidizing composition of the present invention preferably comprise an organopolysiloxane wherein at least one silicium atom is linked to an alkylene group having a hetero-atom, in particular a nitrogen atom, with a poly-(N-acyl alkyleneimine) units of the formula

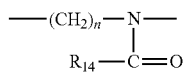

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

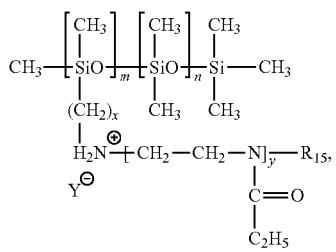

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Compositions may further comprise at least one ubiquinone of the formula

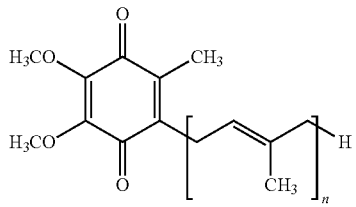

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition.

The composition comprises ubiquinone which is preferably selected from the ones where n is a number between 6 and 10 and more preferably it is ubichinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total composition.

Aqueous composition can comprise further ceramide type of compound at a concentration 0.01 to 3%, preferably 0.05 to 2.5% and more preferably 0.1 to 2% and most preferably 0.1 to 1.5% by weight calculated to total of each composition, with the general formula

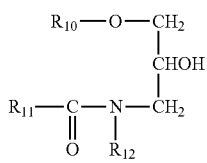

where $R_{10}$ and $R_{11}$ are independent from each other alkyl- or alkenyl group with 10 to 22 carbon atoms and $R_{12}$ is alkyl or hydroxyl alkyl with 1 to 4 carbon atoms group. Preferred compound according to the above chemical structure is cetyl-PG-hydroxyethyl palmitamide.

Aqueous composition preferably comprise at least one diamine compound. Preferred diamide compounds are according to the general structure

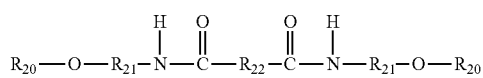

wherein $R_{20}$ is a linear or branched, saturated or unsaturated alkyl chain with 1 to 12 C atoms which may be substituted with hydroxy and/or alkoxy groups, preferably $R_{20}$ is linear or branched, saturated or unsaturated alkyl chain with 1 to 12 C atoms which may be substituted by 1 to 3 substituents selected from a hydroxy group and C1 to C6 alkoxy group, more preferably $R_{20}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{21}$ is linear or branched alkyl chain with 1 to 5 C atoms, preferably linear or branched alkyl chain with 2 to 5 C atoms and more preferably an alkyl chain with 2 to 3 C atoms, and $R_{22}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

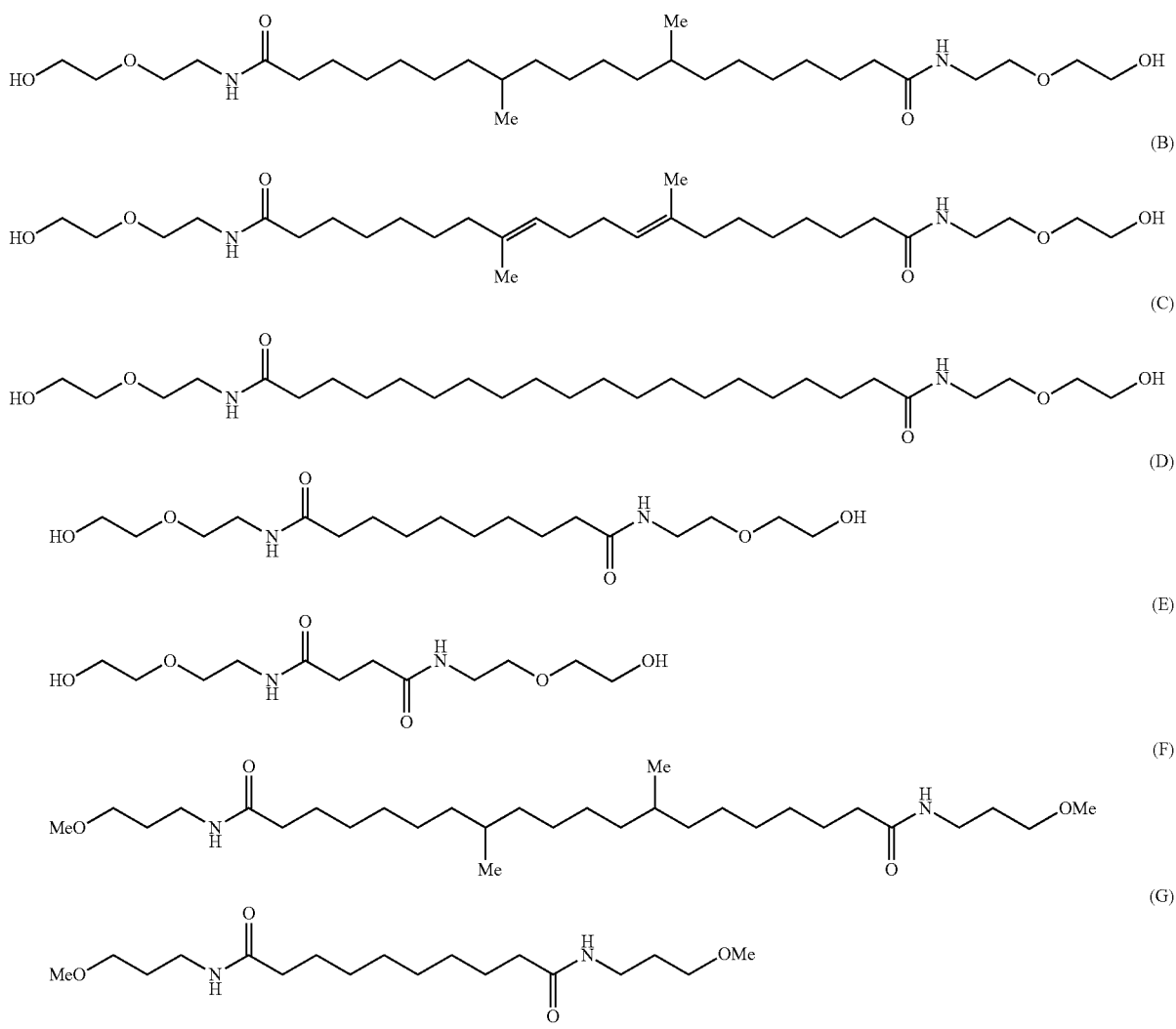

Particularly preferred diamide compound is the compound F which is bis (methoxypropylamido) isodocosane and commercially available from Kao Corporation-Japan.

Concentration of diamide compound is in the range of 0.001 to 5%, preferably 0.002 to 3% more preferably 0.005 to 2% and most preferably 0.01 to 1% by weight calculated to total composition.

Compositions of the present invention may have any consistency. Since the problems related to instability is aggravated in compositions having higher consistency, preferably the compositions of the present invention has a viscosity above or equal to 2000 mPa·s, more preferably 5000 to 25000 mPa·s and most preferably 7500 to 25000 mPa·s and in particular 10000 to 18000 mPa·s measured at 20° C. with a rotation viscosimetre.

Compositions may further comprise substances found customarily in such compositions which are not disclosed above.

Present invention also relates to hair colouring and permanent shaping processes wherein aqueous oxidizing composition of the present invention is used as the oxidizing agent.

Accordingly, present invention is on a hair colouring process wherein a composition comprising at least one hair dye and at least one alkalizing agent is mixed with aqueous oxidizing composition of the present invention and applied onto hair and after processing 1 to 45 min, rinsed off from hair with water and hair is optionally dried.

Permanent shaping process involving the use of an aqueous oxidizing composition of the present invention is carried out wherein hair is first shampooed and an aqueous reducing composition comprising at least one reducing composition is applied and after processing 1 to 30 min rinsed off from hair and hair is applied aqueous oxidizing composition of the present invention and after processing of 1 to 20 min rinsed off. In case that the intention is curling the hair, hair is put on curlers prior to, during or after application of the reducing composition onto hair and removed from hair prior to, during or after application or even after rinsing of the aqueous oxidizing composition.

The following examples are used to illustrate the invention but not to limit it.

EXAMPLE 1

|  | % by weight | | | | | |
| --- | --- | --- | --- | --- | --- | --- |
|  | A | B | C | D | E | F |
| Hydrogen peroxide | 12.0 | 12.0 | 12.0 | 12.0 | 12.0 | 12.0 |
| Propylene glycol | 5.0 | 5.0 | 5.0 | 5.0 | 5.0 | 5.0 |
| Parafin oil | 5.0 | 5.0 | 5.0 | 5.0 | 5.0 | 5.0 |
| Cetearyl alcohol | 5.0 | 5.0 | 5.0 | 5.0 | 5.0 | 5.0 |
| Ceteareth-30 | 2.5 | 2.5 | 2.5 | 2.5 | 2.5 | 2.5 |
| Cetrimonium chloride | 1.0 | 1.0 | 1.0 | 1.0 | 1.0 | 1.0 |
| Phosphoric acid | | | q.s. to pH 2.0 | | | |
| EDTA | 0.1 | 0.1 | 0.1 | 0.1 | 0.1 | 0.1 |
| Magnesium sulphate | — | 2.0 | 1.5 | 1.75 | 1.25 | 2.0 |
| Salicylic acid | — | — | 0.02 | — | 0.05 | 0.05 |
| Acetaminophen | — | — | — | 0.02 | 0.02 | 0.02 |
| Oxyquinoline sulphate | — | — | — | 0.02 | — | 0.02 |
| Water | | | q.s. to pH 2.0 | | | |

All of the above compositions are emulsions and were prepared by conventional method. Viscosity of the compositions was approximately 22000 mPa·s measured at 20° C. with a Brookfield rotation viscosimeter using Spindle 5 at 5 rpm.

The above compositions were filled into PET bottles and stored at 40° C. and 50° C. for several months. After each month, stability was assessed visually by observing the bottle shape. Swelling of the bottle was assessed as:

1 No swelling at all, bottle kept its original shape

2 Slight shape change at the bottom of the bottle but bottle still stands on the table 3 Shape change at the bottom of the bottle but bottle still stands on the table 4 Clear shape change at the bottom of the bottle but bottle cannot stands on the table 5 Bottom of the bottle is almost rounded up and in no was bottle may stand on the table Results of the stability test are given in the following Table.

|  | Composition | | | | | |
| --- | --- | --- | --- | --- | --- | --- |
|  | A | | B | | C | |
| Storage period | 40° C. | 50° C. | 40° C. | 50° C. | 40° C. | 50° C. |
| Start | 1 | 1 | 1 | 1 | 1 | 1 |
| 1 month | 2 | 3 | 1 | 1 | 1 | 2 |
| 2 months | 3 | 3-4 | 1 | 1-2 | 1 | 1 |
| 3 months | 4 | 5 | 1 | 2 | 1 | 1-2 |

|  | Composition | | | | | |
| --- | --- | --- | --- | --- | --- | --- |
|  | D | | E | | F | |
| Storage period | 40° C. | 50° C. | 40° C. | 50° C. | 40° C. | 50° C. |
| Start | 1 | 1 | 1 | 1 | 1 | 1 |
| 1 month | 1 | 1 | 1 | 1 | 1 | 1 |
| 2 months | 1 | 1 | 1 | 1-2 | 1 | 1 |
| 3 months | 1 | 2 | 1-2 | 2 | 1 | 1 |

From the above result it is clear that magnesium sulphate improves peroxide stability. Additionally using salicylic acid, acetaminophen or oxyquinoline sulphate improves peroxide stability further.

In addition to the above findings, it was noted that no major viscosity change was observed.

EXAMPLE 2

Oxidizing composition B of the example 1 was mixed with a hair dyeing composition below at a weight ratio of 1 to 1 and hair tresses were coloured with the resulting composition for 30 min at ambient temperature. Homogeneous colouring was observed.

|  | % by weight |
| --- | --- |
| p-toluenediamine sulphate | 0.8 |
| 4-Chlorresorcinol | 0.3 |
| Resorcinol | 0.1 |
| m-aminophenol | 0.1 |
| Cetearyl alcohol | 4.0 |
| Ceteareth-20 | 3.0 |
| Ammonia 25% | 8.0 |
| Water | to 100 |

EXAMPLE 3

|  | % by weight |
| --- | --- |
| Hydrogen peroxide | 2 |
| Magnesium sulphate | 2 |
| Phosphoric acid | q.s. to pH 3.0 |
| Water | q.s. to 100 |

Alkaline Permanent Wave Composition

|  | % by weight |
| --- | --- |
| Ammonium thioglycolate (60%) | 21.3 |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Luvigel Advanced | 0.5 |
| Perfume | 0.4 |
| Ammonia, 25% | ad pH 8.3 |
| Water | ad 100.0 |

With these compositions the hair was permanently waved according to the process as follows: Hair was shampooed and towel dried and wound on curlers and the reducing composition of above was applied onto hair and after processing of 20 min at ambient temperature rinsed off from hair and subsequently the oxidizing composition was applied and after processing of 10 min rinsed off from hair and curlers were taken off from hair. It was observed that hair was effectively permanently waved and had still natural soft and smooth tough and had natural shine.

For comparative purpose, an additional hair tress was permanently waved as disclosed above, however, as oxidizing composition a composition without magnesium sulfate was used. It was observed that the tress was effectively waved but felt less soft and smooth and had less shine when compared to the tress waved with composition comprising magnesium sulfate in the oxidizing composition.

The invention claimed is:

1. A composition comprising
a) at least one oxidizing agent,
b) at least one magnesium salt present at concentration of 0.5 to 15% by weight, calculated to total of the composition,
c) one or both of
   i. fatty alcohol present at concentration of 1 to 25% by weight, calculated to total of the composition, and
   ii. oil present at concentration of 0.1 to 25% by weight, calculated to total of the composition, and
d) one or more surfactants,
wherein the composition is an aqueous emulsion and has a pH between 1 and 5.

2. The composition according to claim 1, wherein the at least one magnesium salt is selected from magnesium aluminium borosilicate, magnesium aspartate, magnesium borate, magnesium bromate, magnesium bromide, magnesium benzoate, magnesium acetate, magnesium carbonate, magnesium citrate, magnesium clorate, magnesium dihydrogen phosphate, magnesium fluoride, magnesium formate, magnesium hydroxide, magnesium iodide, magnesium lactate, magnesium mandalate, magnesium monofluorophosphate, magnesium oxalate, magnesium oxide, magnesium perborate, magnesium phosphate, magnesium propionate, magnesium pyrophosphate, magnesium salicylate, magnesium silicate, magnesium chloride, magnesium sulfate, magnesium nitrate and magnesium tartarate.

3. The composition according to claim 1, wherein the at least one magnesium salt is magnesium sulfate.

4. The composition according to claim 1, wherein it comprises at least 45% by weight water, calculated to total of the composition.

5. The composition according to claim 2, wherein the at least one oxidizing agent comprises hydrogen peroxide at a concentration of 0.1 to 25% by weight, calculated to total of the composition.

6. The composition according to claim 1, further comprising one or more additional peroxide stabilizing agents, selected from the group consisting of salicylic acid, a salt of salicylic acid, acetaminophen, oxyquinolone, and a salt of oxyquinolone, at a total concentration of 0.001 to 1% by weight, calculated to the total composition.

7. The composition according to claim 1, further comprising at least one thickening agent.

8. The composition according to claim 1, wherein the one or more surfactants is selected from anionic, non-ionic and cationic surfactants, wherein the anionic surfactant is selected from alkyl sulphate and alkyl ether sulphate surfactants, non-ionic surfactant is selected from ethoxylated fatty alcohols, and cationic surfactants are selected from compounds according to general structure

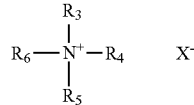

where $R_3$ is a saturated or unsaturated, branched or linear alkyl chain with 8-22 C atoms or

where $R_7$ is saturated or unsaturated, branched or linear alkyl chain with 7-21 C atoms and n has typical value of 1 - 4 or

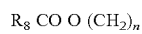

where $R_8$ is saturated or unsaturated, branched or linear alkyl chain with 7-21 C atoms and n has typical value of 1 - 4, and $R_4$, $R_5$ and $R_6$ are lower alkyl chain with 1 to 4 Carbon atoms which may be substituted with one or more OH groups, and X is chloride, bromide, methosulfate.

9. The composition according to claim 1, further comprising one or more of the substances selected from a-) organopolysiloxane wherein at least one silicium atom is linked to an alkylene group having a nitrogen atom, with a poly-(N-acyl alkyleneimine) units of the formula

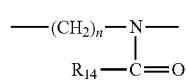

wherein n is a number from 1 to 5 and $R_{14}$ is hydrogen, a $C_1$-$C_{12}$-alkyl or cycloalkyl, aralkyl or aryl group, b-) ubiquinone of the formula

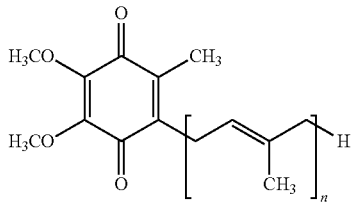

where n is a number between 1 and 10 c-) ceramide of the with the general structure

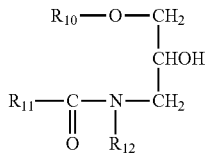

where $R_{10}$ and $R_{11}$ are independent from each other alkyl- or alkenyl group with 10 to 22 carbon atoms and $R_{12}$ is alkyl or hydroxyl alkyl with 1 to 4 carbon atoms group, and d-) diamide compounds according to the general structure

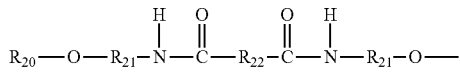

wherein $R_{20}$ is linear or branched, saturated or unsaturated alkyl chain with 1 to 12 C atoms which may be substituted by 1 to 3 substituents selected from a hydroxy group and C1 to C6 alkoxy group, $R_{21}$ is linear or branched alkyl chain with 2 to 5 C atoms and an alkyl chain with 2 to 3 C atoms, and $R_{22}$ is linear or branched, saturated or unsaturated alkyl chain with 11 to 22 C atoms.

10. Process for colouring hair wherein a composition comprising at least one hair dye and at least one alkalizing agent is mixed with the composition according to claim 1 and applied onto hair and after processing 1 to 45 min, rinsed off from hair with water and hair is optionally dried.

11. Process for permanent of shaping hair wherein hair is shampooed and an aqueous composition comprising at least one reducing agent is applied onto hair and after processing 1 to 30 min rinsed off from hair and thereafter, the composition according to claim 1 is applied to the hair, and after processing of 1 to 20 min rinsed off.

12. The composition according to claim 1, wherein the oil is present at a concentration between 1 to 20% by weight, calculated to total of the composition.

13. The composition according to claim 12, wherein the oil is present at a concentration of 2.5 to 15% by weight, calculated to total of the composition.

\* \* \* \* \*